(12) United States Patent
Miller et al.

(10) Patent No.: US 8,268,874 B2
(45) Date of Patent: Sep. 18, 2012

(54) ANTI-CANCER COMPOUNDS, SYNTHESIS THEREOF, AND METHODS OF USING SAME

(75) Inventors: Marvin J. Miller, Mishiwaka, IN (US); Garrett C. Moraski, South Bend, IN (US); Jonathan Stefely, South Bend, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 12/920,808

(22) PCT Filed: Mar. 3, 2009

(86) PCT No.: PCT/US2009/035920
§ 371 (c)(1),
(2), (4) Date: Sep. 2, 2010

(87) PCT Pub. No.: WO2009/111502
PCT Pub. Date: Sep. 11, 2009

(65) Prior Publication Data
US 2011/0021574 A1    Jan. 27, 2011

Related U.S. Application Data

(60) Provisional application No. 61/067,900, filed on Mar. 3, 2008.

(51) Int. Cl.
*A61K 31/422* (2006.01)
*C07D 263/34* (2006.01)
(52) U.S. Cl. ........................ 514/374; 548/236
(58) Field of Classification Search .............. 514/340, 514/374, 359; 435/325, 366; 548/236, 255; 546/268.4
See application file for complete search history.

(56) References Cited

U.S. PATENT DOCUMENTS

| | | | |
|---|---|---|---|
| 7,189,712 B2 | 3/2007 | Brown et al. | |
| 2009/0036450 A1* | 2/2009 | Takagi et al. | 514/236.5 |

FOREIGN PATENT DOCUMENTS

| | | |
|---|---|---|
| WO | WO03059907 A1 | 7/2003 |
| WO | WO2004026863 A1 | 4/2004 |
| WO | WO2006032520 A1 | 3/2006 |

OTHER PUBLICATIONS

Galli, Ubaldina et al., "Synthesis and Biological Evaluation of Isoteric Analogues of FK866, an Inhibitor of NAD Salvage," ChemMedChem 2008, vol. 3, pp. 771-779.
Leeb, Laurin et al., "Optimization of Click Chemistry Using Azide and Alkyne Scavenger Resins," QSAR Comb. Sci., 2007, vol. 26, No. 11-12, pp. 1145-1150.
Riva, Raphael et al., "Synthesis of New Substituted Lactones by 'Click' Chemistry," ARKIVOC 2007, pp. 292-306.
Lee, Bo-Young et al., "A New Solvent System for Efficient Synthesis of 1,2,3-Triazoles," Tetrahedron Letters 2006, vol. 47, pp. 5105-5109.
Manley, Paul W. et al., "Therapies Directed at Vascular Endothelial Growth Factor," Expert Opin. Investig. Drugs, 2002, vol. 11(12), pp. 1715-1736.
Davies, Thomas G. et al., "Structure-Based Design of Cyclin-Dependent Kinase Inhibitors," Pharmacology & Therapeutics, 2002, vol. 93, pp. 125-133.
Toogood, Peter L., "Cyclin-Dependent Kinase Inhibitors for Treating Cancer," Medicinal Research Reviews, 2001, vol. 21, No. 6, pp. 487-498.
Tai, Vincent W. F. et al., "Discovery and Structure-Activity Relationship of 2-Phenyl-Oxazole-4-Carboxamide Derivatives as Potent Apoptosis Inducers," Bioorganic & Medicinal Chemistry Letters, 2006, vol. 16, pp. 4554-4558.

* cited by examiner

*Primary Examiner* — Kristin Bianchi
(74) *Attorney, Agent, or Firm* — Schwabe, Williamson & Wyatt

(57) ABSTRACT

Embodiments relate to the field of chemistry and biochemistry, and, more specifically, to anti-cancer compounds, synthesis thereof, and methods of using same. Disclosed herein are various heterocyclic compounds and methods of using the novel anti-cancer compounds to inhibit the growth of a cancer cell, for instance a leukemia, non-small cell lung, central nervous system (CNS), skin, ovarian, renal, prostate, breast, or colon cancer cell. Other embodiments include methods of treating cancer in a subject, such as using the disclosed heterocyclic anti-cancer agents.

7 Claims, 6 Drawing Sheets

ANTI-CANCER COMPOUNDS, SYNTHESIS THEREOF, AND METHODS OF USING SAME

CROSS REFERENCE TO RELATED APPLICATIONS

The present application claims priority to U.S. Provisional Patent Application No. 61/067,900, filed Mar. 3, 2008, entitled "SYNTHESIS OF ANTI-CANCER COMPOUNDS CONTAINING OXAZOLE AND TRIAZOLE GROUPS AND METHODS OF USING SAME," the disclosure of which is hereby incorporated by reference in its entirety.

GOVERNMENT INTERESTS

This invention was made with Government support under Grant RO1 AI054193 awarded by the National Institutes of Health. The Government has certain rights in the invention.

TECHNICAL FIELD

Embodiments herein relate to the field of chemistry and biochemistry, and, more specifically, to anti-cancer compounds, synthesis thereof, and methods of using same.

BACKGROUND

Microtubules, dynamic protein polymers composed of α-tubulin and β-tubulin heterodimers, are a well-established cellular target for anti-cancer drugs. Dynamic polymerization and depolymerization of tubulin heterodimers is a necessary and tightly controlled process during mitosis. Perturbing microtubule dynamics with small molecules blocks the cell cycle in the metaphase/anaphase transition and leads to apoptosis. Therefore, molecules that target tubulin may be used to halt the uncontrolled cell division that characterizes cancer cells. This therapeutic strategy was validated by the success of antimitotic drugs such as paclitaxel, docetaxel, vincristine, and vinblastine, but the clinical utility of these drugs is limited by neurotoxicity and p-glycoprotein-mediated drug resistance. Synthetic taxanes, vinca alkaloid analogs, and novel chemotypes that modulate microtubule dynamics have been synthesized in an attempt to overcome these limitations, but few have produced useful results during clinical trials.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
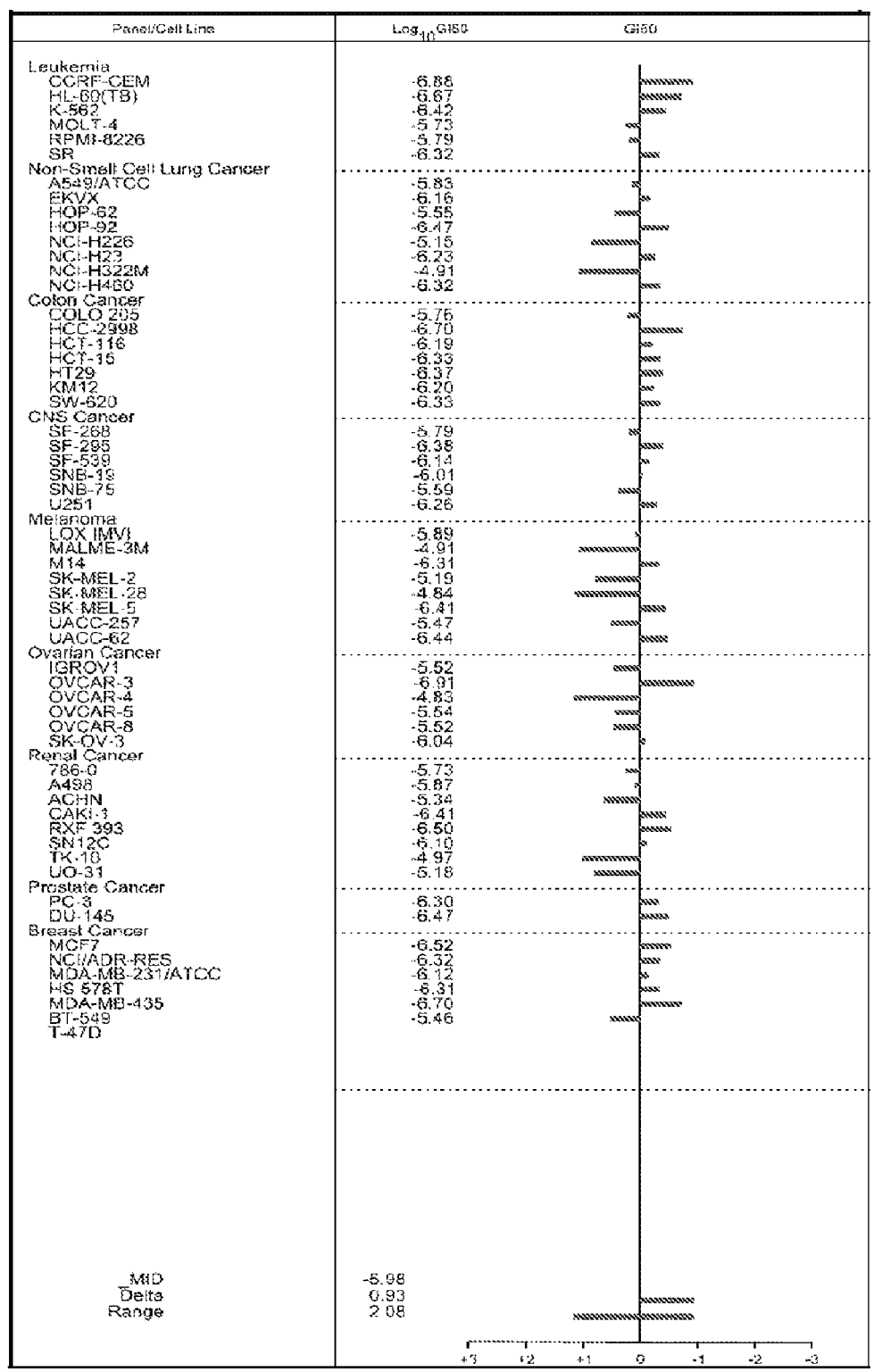
FIG. 1 illustrates a mean graph of activity of 1,2,3-triazole 9c (ND-6732) for all 60 cell lines in the National Cancer Institute (NCI) Assay, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

As used herein, the term "halogen" refers to fluoro, bromo, chloro and iodo substituents.

As used herein, the term "alkyl" refers to a cyclic, branched, or straight chain alkyl group containing only carbon and hydrogen, and unless otherwise mentioned contains one to twelve carbon atoms. This term may be further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, for instance, halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

As used herein, the term "substituted alkyl" refers to an alkyl moiety including 1-4 substituents selected from halogen, het, cycloalkyl, cycloalkenyl, aryl, amino, cyano, nitro, —$OQ_{10}$, —$SQ_{10}$, —$S(O)_2Q_{10}$, —$S(O)Q10$, —$OS(O)_2Q_{10}$, —$C(=NQ_{10})Q_{10}$, —$C(=NOQ_{10})Q_{10}$, —$S(O)_2$—N=$S(O)(Q_{10})_2$, —$S(O)_2$—N=$S(Q_{10})_2$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(S)NQ_{10}Q_{10}$, —$N(Q_{10})C(S)NQ_{10}Q_{10}$, —$C(O)NQ_{10}Q_{10}$, —$C(S)NQ_{10}Q_{10}$, —$C(O)C(Q_{16})_2OC(O)Q_{10}$, —CN, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, and —$SNQ_{10}Q_{10}$. Each of the het, cycloalkyl, cycloalkenyl, and aryl being optionally substituted with 1-4 substituents independently selected from halogen and $Q_{15}$.

As used herein, the term "cycloalkyl" refers to a cyclic alkyl moiety. Unless otherwise stated, cycloalkyl moieties include between 3 and 8 carbon atoms.

As used herein, the term "alkene" refers to a hydrocarbon molecule with the general formula CH that contains one or more double bonds.

As used herein, the term "alkyne" refers to a moiety having the general formula $C_2H_{2n-2}$ corresponding to carbon chains with a triple carbon-carbon bond included.

As used herein, the term "alcohol" refers to an organic compound that has the general formula $C_nH_{2n}+1OH$, consisting of hydrocarbon chains terminated by hydroxyl groups, O—H.

As used herein, the term "epoxide" refers to any of a class of organic compound, cyclic ethers, having a three-member ring.

As used herein, the term "ketone" refers to an organic compound containing the carbonyl group, >C=O, to which other carbon atoms are attached.

As used herein, the term "ester" refers to the product of the reaction between a carboxylic acid and an alcohol.

As used herein, the term "ether" refers to an organic compound containing the functional group RO—R'.

As used herein, the term "aldehyde" refers to an organic compound containing a —CHO group.

As used herein, the term "nitrile" refers to any of a class of organic compounds containing the cyano radical —CN.

As used herein, the term "thiol" refers to a molecular group that includes a bonded sulfur and hydrogen atom (—SH).

As used herein, the term "thioester" refers to a compound resulting from the bonding of sulfur with an acyl group with the general formula R—S—CO—R'. Thioesters are the product of esterification between a carboxylic acid and a thiol (as opposed to an alcohol in regular esters).

As used herein, the term "sulfide" refers to an organic compound containing sulfur bonded to carbon. The term "disulfide" refers to the structural unit composed of a linked pair of sulfur atoms.

As used herein, the term "sulfone" refers to a chemical compound containing a sulfonyl functional group attached to two carbon atoms. The central sulfur atom is twice double bonded to oxygen and has two further hydrocarbon substituents. The general structural formula is R—S(=O)(=O)—R' where R and R' are the organic groups.

As used herein, the term "sulfoxide" refers to a chemical compound containing a sulfinyl functional group attached to two carbon atoms. Sulfoxides can be considered oxidized sulfides.

As used herein, the term "amino" refers to $NH_2$, NHR, or $NR_2$. Unless otherwise stated R can be alkyl, alkenyl, alkynyl, cycloalkyl, cycloalkenyl, het or aryl.

As used herein, the term "amide" refers to an organic compound containing the —$CONH_2$— group.

As used herein, the term "urea" refers to an organic compound with the chemical formula $(NH_2)_2CO$.

As used herein, the term "carbamate" refers to any of a group of organic compounds sharing a common functional group with the general structure —NH(CO)O—. Carbamates are esters of carbamic acid, $NH_2COOH$. Since carbamic acid contains nitrogen attached to a carboxyl group, it is also an amide. Therefore, carbamate esters may have alkyl or aryl groups substituted on the nitrogen, or the amide function. For example, ethyl carbamate is unsubstituted, whereas ethyl N-methylcarbamate has a methyl group attached to the nitrogen.

As used herein, the term "nitro" refers to $NO_2$.

As used herein, the term "aryl" refers to phenyl and naphthyl.

As used herein, the term "morpholine" refers to an organic chemical compound having the chemical formula $O(CH_2CH_2)_2NH$. This heterocycle features both amine and ether functional groups. Because of the amine, morpholine is a base; its conjugate acid is called morpholinium. For example, when morpholine is neutralized by hydrochloric acid, one obtains the salt morpholinium chloride.

As used herein, the term "thiomorpholine" refers to $C_4H_9NS$, is a heterocyclic compound containing nitrogen and sulfur. It may be considered a thio derivative of morpholine.

As used herein, the term "piperazine" refers to an organic compound that consists of a six-member ring containing two opposing nitrogen atoms.

As used herein, the term "piperidine" refers to an organic compound with the molecular formula $(CH_2)_5NH$. This heterocyclic amine consists of a six-member ring containing five methylene units and one nitrogen atom.

As used herein, the term "acyl" refers to any of a group or radical of the form RCO— where R is an organic group.

As used herein, the term "furan" refers to any of a class of aromatic heterocyclic compounds containing a ring of four carbon atoms and an oxygen atom; for instance, $C_4H_4O$. As used herein, the term "nitrofuran" refers to a furan ring with a nitro group.

As used herein, the term "thiophene" refers to the heterocyclic compound with the formula $C_4H_4S$. Consisting of a flat five-membered ring, it is aromatic as indicated by its extensive substitution reactions. Related to thiophene are benzothiophene and dibenzothiophene, containing the thiophene ring fused with one and two benzene rings, respectively. Compounds analogous to thiophene include furan ($C_4H_4O$) and pyrrole ($C_4H_4NH$).

As used herein, the term "imidazole" refers to an organic compound with the formula $C_3H_4N_2$. This aromatic heterocyclic is classified as an alkaloid. Imidazole refers to the parent compound whereas imidazoles are a class of heterocycles with similar ring structure but varying substituents.

As used herein, the term "oxazole" refers to a five-member heterocycle having three carbon atoms, one oxygen atom, one nitrogen atom and two double bonds; the 1,3-isomer is aromatic.

As used herein, the tem "oxazoline" refers to an unsaturated heterocyclic compound containing a five-member ring, two double bonds, one nitrogen and one oxygen atom; any derivative of this compound.

As used herein, the term "thiazole" refers to any of a class of unsaturated heterocyclic compounds containing a ring of three carbon atoms, a sulfur and an nitrogen atom; for instance the simplest one, $C_3H_3SN$.

As used herein, the term "thiazoline" refers to an unsaturated heterocyclic compound containing a five-member ring, two double bonds, one nitrogen and one sulfur atom; any derivative of this compound.

As used herein, the term "triazole" refers to either one of a pair of isomeric chemical compounds with molecular formula $C_2H_3N_3$, having a five-member ring of two carbon atoms and three nitrogen atoms.

As used herein, the term "pyridine" refers to any of a class of aromatic heterocyclic compounds containing a ring of five carbon atoms and an nitrogen atom; for instance the simplest one, $C_5H_5N$.

As used herein, the term "pyrazine" refers to a diazine in which the two nitrogen atoms are in the para-position.

As used herein, the term "naphthalene" refers to an aromatic, white, solid hydrocarbon with formula $C_{10}H_8$ and the structure of two fused benzene rings.

As used herein, the term "diketopiperazine" refers to a class of cyclic organic compounds that result from peptide bonds between two amino acids to form a lactam. They are the smallest possible cyclic peptides.

As used herein, the term "quinoline" refers to any of a class of aromatic heterocyclic compounds containing a benzene ring fused with a ring of five carbon atoms and an nitrogen atom; for instance the simplest one, $C_9H_7N$. Isoquinoline, also known as benzo[c]pyridine or 2-benzanine, is a heterocyclic aromatic organic compound. It is a structural isomer of quinoline. Isoquinoline and quinoline are benzopyridines, which are composed of a benzene ring fused to a pyridine ring. In a broader sense, the term isoquinoline is used to make reference to isoquinoline derivatives.

As used herein, the term "oxazolidinone" refers to a class of heterocyclic organic compounds containing both nitrogen and oxygen in a 5-member ring.

As used herein, the term "het" refers to a mono- or bi-cyclic ring system containing one or more heteroatom selected from O, S, and N. Each mono-cyclic ring may be aromatic, saturated or partially unsaturated. A bi-cyclic ring system may include a mono-cyclic ring containing one or more heteroatom fused with a cycloalkyl or aryl group. A bi-cyclic ring system may also include a mono-cyclic ring containing one or more heteroatom fused with another het, mono-cyclic ring system.

Examples of "het" include but are not limited to pyridine, thiophene, furan, pyrazoline, pyrrole, pyrazoline, pyrimidine, 2-pyridyl, 3-pyridyl, 4-pyridyl, 2-pyrimidinyl, 4-pyrimidinyl, 5-pyrimidinyl, 3-pyrazinyl, 3-pyridazinyl, 4-pyridazinyl, 4-oxo-2-imidazolyl, 1,2,4-oxadiazole, 1,3,4-oxadiazole, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,5-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo [2.2.1]heptyl.

As used herein, the term "heteroaryl" refers to a mono- or bicyclic het in which one or more cyclic ring is aromatic.

As used herein, the term "substituted heteroaryl" refers to a heteroaryl moiety substituted with one or more functional groups selected from halogen, alkyl, hydroxyl, amino, alkoxy, cyano, and nitro.

As used herein, the term "substituted aryl" refers to an aryl moiety having 1-3 substituents selected from halogen, het, alkyl, substituted alkyl, alkenyl, alkynyl, alkoxy, cycloalkyl, cycloalkenyl, aryl, cyano, nitro, $-OQ_{10}$, $-SQ_{10}$, $-S(O)_2Q_{10}$, $-S(O)Q_{10}$, $-OS(O)_2Q_{10}$, $-C(=NQ_{10})Q_{10}$, $-C(=NOQ_{10})Q_{10}$, $-S(O)_2-N=S(O)(Q_{10})_2$, $-S(O)_2-N=S(Q_{10})_2$, $-NQ_{10}Q_{10}$, $-C(O)Q_{10}$, $-C(S)Q_{10}$, $-C(O)OQ_{10}$, $-OC(O)Q_{10}$, $-C(O)NQ_{10}Q_{10}$, $-C(S)NQ_{10}Q_{10}$, $-C(O)C(Q_{16})_2OC(O)Q_{10}$, $-NQ_{10}C(O)Q_{10}$, $-N(Q_{10})C(S)NQ_{10}Q_{10}$, $-N(Q_{10})C(S)Q_{10}$, $-NQ_{10}C(O)NQ_{10}Q_{10}$, $-S(O)_2NQ_{10}Q_{10}$, $-NQ_{10}S(O)_2Q_{10}$, $-NQ_{10}S(O)Q_{10}$, $-NQ_{10}SQ_{10}$, and $-SNQ_{10}Q_{10}$. The het, cycloalkyl, cycloalkenyl, alkenyl, alkynyl, and aryl being optionally substituted with 1-3 substituents selected from halogen and $Q_{15}$.

Each $Q_{10}$ is independently selected from H, alkyl, cycloalkyl, het, cycloalkenyl, and aryl. The het, cycloalkyl, cycloalkenyl, and aryl being optionally substituted with 1-3 substitutuents selected from halo and $Q_{13}$.

Each $Q_{11}$ is independently selected from H, halogen, alkyl, aryl, cycloalkyl, and het. The alkyl, aryl, cycloalkyl, and het being optionally substituted with 1-3 substituents independently selected from halogen, nitro, cyano, $=S$, $=O$, and $Q_{14}$.

Each $Q_{13}$ is independently selected from $Q_{11}$, $-OQ_{11}$, $-SQ_{11}$, $-S(O)_2Q_{11}$, $-S(O)Q_{11}$, $-OS(O)_2Q_{11}$, $-C(=NQ_{11})Q_{11}$, $-S(O)_2-N=S(O)(Q_{11})_2$, $-S(O)_2-N=S(Q_{11})_2$, $-SC(O)Q_{11}$, $-NQ_{11}Q_{11}$, $-C(O)Q_{11}$, $-C(S)Q_{11}$, $-C(O)OQ_{11}$, $-OC(O)Q_{11}$, $-C(O)NQ_{11}Q_{11}$, $-(S)NQ_{11}Q_{11}$, $-C(O)C(Q_{16})_2OC(O)Q_{10}$, $-CN$, $=O$, $=S$, $-NQ_{11}C(O)Q_{11}$, $-NQ_{11}C(S)Q_{11}$, $-NQ_{11}C(O)NQ_{11}Q_{11}$, $-NQ_{11}C(S)NQ_{11}Q_{11}$, $-S(Q)_2NQ_{11}Q_{11}$, $-NQ_{11}S(O)_2Q_{11}$, $-NQ_{11}S(O)Q_{11}$, $-NQ_{11}SQ_{11}$, $-NO_2$, and $-SNQ_{11}Q_{11}$.

Each $Q_{14}$ is independently selected from H, alkyl, cycloalkyl, phenyl, or naphthyl, each optionally substituted with 1-4 substituents independently selected from F, Cl, Br, I, $-OQ_{16}$, $-SQ_{16}$, $-S(O)_2Q_{16}$, $-S(O)Q_{16}$, $-OS(O)_2Q_{16}$, $-NQ_{16}Q_{16}$, $-C(O)Q_{16}$, $-C(S)Q_{16}$, $-C(O)OQ_{16}$, $-NO_2$, $-C(O)NQ_{16}Q_{16}$, $-C(S)NQ_{16}Q_{16}$, $-CN$, $-NQ_{16}C(O)Q_{16}$, $-NQ_{16}C(S)Q_{16}$, $-NQ_{16}C(O)NQ_{16}Q_{16}$, $-NQ_{16}C(S)NQ_{16}Q_{16}$, $-S(O)_2NQ_{16}Q_{16}$, and $-NQ_{16}S(O)_2Q_{16}$. The alkyl, cycloalkyl, and cycloalkenyl being further optionally substituted with $=O$ or $=S$.

Each $Q_{15}$ is independently selected from H, alkyl, cycloalkyl, heteroaryl, phenyl, or naphthyl, each optionally substituted with 1-4 substituents independently selected from F, Cl, Br, I, $-OQ_{16}$, $-SQ_{16}$, $-S(O)_2Q_{16}$, $-S(O)Q_{16}$, $-OS(O)_2Q_{16}$, $-C(=NQ_{16})Q_{16}$, $-S(O)_2-N=S(O)(Q_{16})_2$, $-S(O)_2-N=S(Q_{16})_2$, $-SC(O)Q_{16}$, $-NQ_{16}Q_{16}$, $-C(O)Q_{16}$, $-C(S)Q_{16}$, $-C(O)OQ_{16}$, $-OC(O)Q_{16}$, $-C(S)NQ_{16}Q_{16}$, $-C(O)C(Q_{16})_2OC(O)Q_{16}$, $-CN$, $-NQ_{16}C(O)Q_{16}$, $-NQ_{16}C(S)Q_{16}$, $-NQ_{16}C(O)NQ_{16}Q_{16}$, $-NQ_{16}C(S)NQ_{16}Q_{16}$, $-S(O)_2NQ_{16}Q_{16}$, $-NQ_{16}S(O)_2Q_{16}$, $-NQ_{16}S(O)Q_{16}$, $-NQ_{16}SQ_{16}$, $-NO_2$, and $-SNQ_{16}Q_{16}$. The alkyl, cycloalkyl, and cycloalkenyl being further optionally substituted with $=O$ or $=S$.

Each $Q_{16}$ is independently selected from H, alkyl, and cycloalkyl. The alkyl and cycloalkyl optionally including 1-3 halogens.

Embodiments of the present disclosure provide novel anti-cancer agents. Certain embodiments are directed to compounds that contain oxazole and/or triazole groups. In an embodiment, anti-cancer agents are provided that disrupt mitosis. In other embodiments, the anti-cancer agents provided herein may inhibit other biological processes in cancer cells.

In embodiments, the anti-cancer agents of this disclosure may have useful activity against a variety of cancer cells. The in vitro activity of disclosed compounds may be assessed by standard testing procedures, for instance in assays that measure inhibition of the growth of cancer cells or cell lines, such as the NCI anti-cancer drug screening assay.

In embodiments, anti-cancer agents described herein may be useful for treating (for instance, ameliorating or preventing) cancer in a subject. In an embodiment, a compound may be administered to a subject locally or systemically. In embodiments, the anti-cancer agent may be administered parenterally, for instance subcutaneously, intravenously, or by inhalation, or it may be administered topically. The anti-cancer agent may be used alone or in combination with other anti-cancer agents. In an embodiment, the anti-cancer agent may be administered in varying concentrations depending upon the cancer's susceptibility to the anti-cancer agent being applied, the extent of the disease, and the general health of the subject.

In an embodiment, the anti-cancer compound may be incorporated into a pharmaceutical composition. In embodiments, certain anti-cancer agents described herein may be useful for treating cancer, for instance leukemia, non-small cell lung cancer, central nervous system (CNS) cancer, skin cancer, for instance melanoma, ovarian cancer, renal cancer, prostate cancer, breast cancer, or colon cancer in a human or non-human animal subject, such as by administering an effective amount of the anti-cancer compound to the subject.

Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

Pharmaceutical compositions in accordance with embodiments of the disclosure may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds disclosed herein dissolved in water and water-propylene glycol systems, optionally containing suitable conventional coloring agents, flavoring agents, stabilizers, and/or thickening agents.

In an embodiment, a pharmaceutical composition may be provided employing conventional techniques in unit dosage form containing effective or appropriate amounts of one or more active component. In embodiments, the quantity of active component (compound) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

In embodiments, in therapeutic use for treating, ameliorating, preventing, or combating cancer in animals, the compounds or pharmaceutical compositions thereof may be administered orally, parenterally, topically, and/or by inhalation at a dosage to obtain and maintain a concentration or blood-level of active component in the animal undergoing treatment that is therapeutically effective. In an embodiment, such a therapeutically effective amount of dosage of active component may be in the range of about 0.1 to about 100 mg/kg, more preferably about 3.0 to about 50 mg/kg, of body weight/day. It is to be understood that the dosages may vary depending upon the requirements of the patient, the severity, type, stage, grade, or location of the cancer being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose also may be divided into multiple doses for administration, for instance, two to four times per day.

In an embodiment, an initial antimitotic, anti-cancer compound was provided and tested. Such compound is identified below as compound 9c (compound ND-6732). Compound 9c (shown below) is a 1,2,3-triazole derivative of 2-phenyl-oxazole-4-carboxamide, and it inhibits the growth of cancer cells at sub-micromolar concentrations ($GI_{50}$: PC-3=504 nM & MCF7=302 nM), as described herein.

The antimitotic compounds described herein were derived from work on Mycobactin S (1; see below), a natural product that exhibits anti-tuberculosis activity and is produced by *Mycobacterium smegmatis*. During synthesis of Mycobactin S, all synthetic intermediates were screened for biological activity. Surprisingly, benzyl ester (2), a small fragment of the natural product, exhibited anti-tuberculosis activity with potency similar to that of Mycobactin S. While exploring derivatives of 2, it was found that 2-phenyl-oxazole-4-carboxamide 3 also was active against *M. tuberculosis*.

Shown below is the synthetic evolution of a natural product fragment: two dimensional structural representations of anti-tuberculosis compounds 2 and 3 and anti-cancer compound 9c (ND-6732), all derived from a fragment of natural product 1, Mycobactin S. MIC values indicate in vitro anti-tuberculosis activity against *M. tuberculosis* H37Rv in a standard GAST assay, and the $IC_{50}$ value indicates in vitro anti-cancer activity against human breast cancer cell line MCF-7.

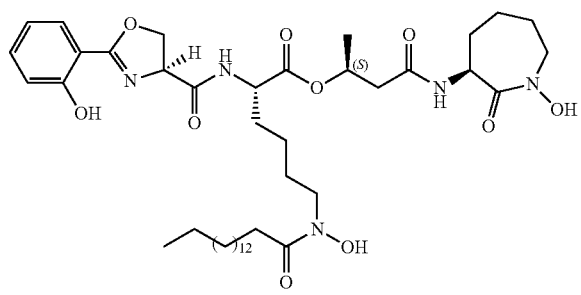

MIC (TB) = 3.9 μM

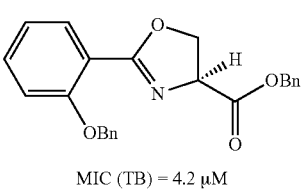

MIC (TB) = 4.2 μM

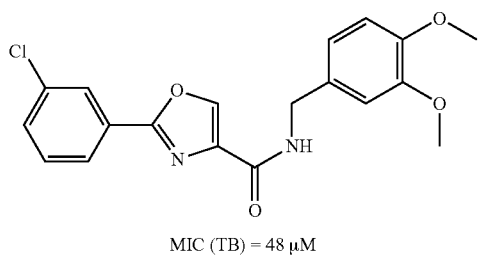

MIC (TB) = 48 μM

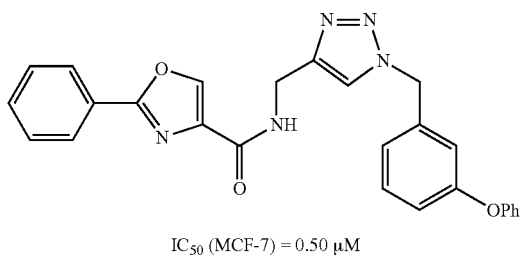

IC$_{50}$ (MCF-7) = 0.50 μM

Surprisingly, synthesizing new 2-phenyl-oxazole-4-carboxamides generated a novel class of chemotherapeutic anti-cancer agents. Described herein are the synthesis and structure-activity relationships of several 1,2,3-triazole derivatives of the 2-phenyl-oxazole-4-carboxamide fragment which exhibit potent anti-cancer activity. Also described are mode of action studies based on in silico and in vitro work, which demonstrate that these triazoles represent a new antimitotic chemotype.

In embodiments, the exemplary compounds described above may be synthesized according to the following general procedures. The strategy for exploring the chemical space around the 2-phenyl-oxazole-4-carboxamide fragment was based on "click chemistry." More specifically, the Cu(I)-catalyzed azide-alkyne cycloaddition (CuAAC) reaction was chosen. The CuAAC reaction produces 1,2,3-triazoles by linking terminal alkynes to organic azides, so one of these two functional groups was installed onto the 2-phenyl-oxazole-4-carboxamide. Given the presence of an amide bond in the fragment, a terminal alkyne was installed to form the desired amide bond by condensation of propargyl amine with 2-phenyl-oxazole-4-carboxylic acid.

Triazole derivatives of the 2-phenyl-oxazole-4-carboxamide fragment were synthesized using the CuAAC reaction according to the protocols shown in Scheme 1. β-hydroxy amides 5a-c were synthesized through EDC-mediated coupling of benzoic acid derivatives 4a-c to the benzyl ester of serine. One-pot dehydrative cyclization and oxidation of the β-hydroxy amides with diethylaminosulfurtrifluoride (DAST) and DBU/BrCCl$_3$ yielded oxazoles 6a-c. Catalytic hydrogenation of the benzyl esters provided carboxylic acids 7a-c. Carbodiimide coupling of 7a-c with propargyl amine produced terminal alkynes 8a-c. In a separate synthetic pathway, a series of benzyl azides, 11a-d, was synthesized by treating the corresponding benzyl bromides 10a-d with sodium azide in DMSO (Scheme 2). As necessary, the benzyl bromides were synthesized from alcohols. In the convergent synthetic step, mixing terminal alkynes 8a-c with benzyl azides 11a-d in the presence of a catalytic amount of Cu(I) efficiently and regioselectively produced 1,4-substituted triazoles 9a-l. Aqueous CuAAC conditions (H$_2$O/t-BuOH, 2:1) were utilized instead of organic reaction conditions because the aqueous conditions facilitated precipitation of the products with high purity.

Scheme 1. Synthesis of antimitotic triazoles 9a-l.

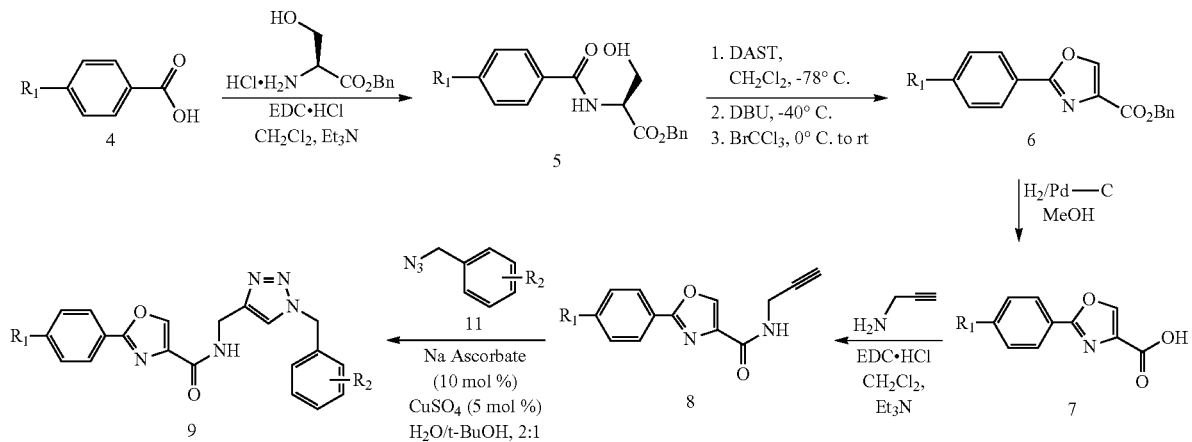

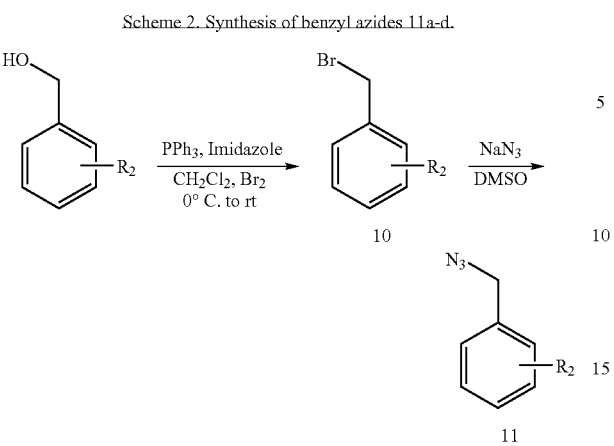

Structure-activity relationship studies later demonstrated that the 2-aryl-4-carboxamide oxazole could be replaced by a relatively simple aryl carboxamide. The synthesis of aryl carboxamide derivative 14 utilized a commercially available aryl acid (Scheme 3), which allowed access to an anti-cancer 1,2,3-triazole without the need to go through the three step synthesis of the 2-phenyl-oxazole-4-carboxamide. The simplicity of reaction Scheme 3 shows that a large library of 1,2,3-triazole-based anti-cancer compounds could be quickly synthesized with combinatorial chemistry techniques and based on the present disclosure.

Cancers are classified by the type of cell that the tumor resembles and, therefore, the tissue presumed to be the origin of the tumor. For example, carcinomas are malignant tumors derived from epithelial cells. This group represents the most common cancers, including the common forms of breast, prostate, lung, and colon cancer. Lymphomas and leukemias include malignant tumors derived from blood and bone marrow cells. Sarcomas are malignant tumors derived from connective tissue or mesenchymal cells. Mesotheliomas are tumors derived from the mesothelial cells lining the peritoneum and the pleura. Gliomas are tumors derived from glia, the most common type of brain cell. Germinomas are tumors derived from germ cells, normally found in the testicle and ovary. Choriocarcinomas are malignant tumors derived from the placenta. Several specific, non-limiting examples of cancer cells which are inhibited by the compounds disclosed herein include CNS cancer cells such as neuroblastoma cells, renal cell cancer cells, melanoma cells, leukemia cells, colon cancer cells, breast cancer cells, ovarian cancer cells, prostate cancer cells, and non-small cell lung cancer cells.

As discussed above, compounds in accordance with embodiments of the present disclosure are designed to exhibit antimitotic activity. In other embodiments, compounds may be designed to target particular types of cancer cells. Briefly, the method includes providing a cancer cell that responds to antimitotic therapy and contacting the cancer cell with at least one compound having the formula:

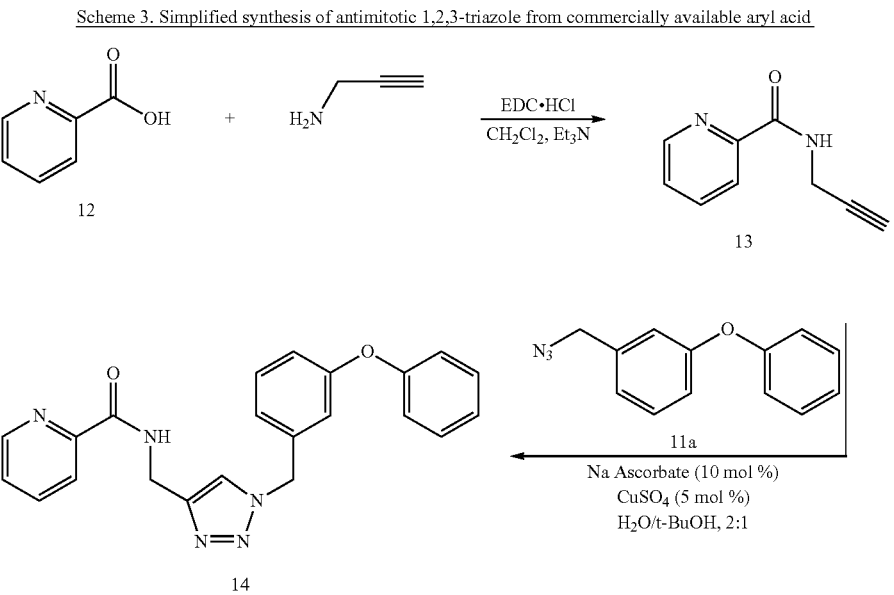

Embodiments of the present disclosure also provide methods for inhibiting the growth of a cancer cell using compounds described herein. As used herein, the term "cancer" refers to any member of a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system.

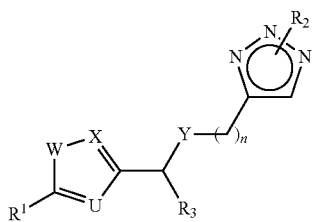

or a pharmaceutically acceptable salt thereof. According to embodiments, $R_1$=H, halogen, alkyl, substituted alkyl, cycloalkyl, functionalized alkyl, cycloheteroalkyl, acyl, halogenated acyl, substituted acyl, aryl, substituted aryl, heteroaryl, substituted heteroaryl, or heterocylic, wherein $R_1$ is mono or polysubstituted; $R_2$=H, alkyl, substituted alkyl, cycloalkyl, functionalized alkyl, aryl, heteroaryl, substituted heteroaryl, or heterocylic, forming a 1,4- or 1,5-disubstitution; $R_3$=H or O; Y=NH, O, or $CH_2$; U, W, and X are each independently selected from C, O, S, NH, and $NR_1$; and n=0, 1, 2, 3, 4, or 5. In some embodiments, the cancer cell is a leukemia, non-small cell lung, central nervous system (CNS), skin, ovarian, renal, prostate, breast, or colon cancer cell. In an embodiment, a source may be a human or an animal and a contacting operation may be performed in vivo in said human or animal, or may be performed in vitro on an extracted sample or testing sample.

For the purposes of further explanation of the language above, a 1,4-disubstituted triazole may appear as follows:

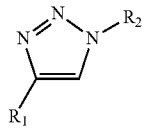

and a 1,5-disubstituted triazole may appear as follows:

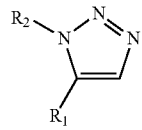

and, therefore, the isomers may collectively be represented as follows

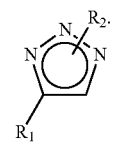

In an embodiment, a further compound may have the formula:

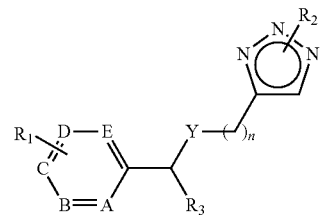

or a pharmaceutically acceptable salt thereof. According to embodiments, $R_1$=H, halogen, alkyl, substituted alkyl, cycloalkyl, functionalized alkyl, cycloheteroalkyl, acyl, halogenated acyl, substituted acyl, aryl, substituted aryl, heteroaryl, substituted heteroaryl, or heterocylic, wherein $R_1$ is mono or polysubstituted; $R_2$=H, alkyl, substituted alkyl, cycloalkyl, functionalized alkyl, aryl, heteroaryl, substituted heteroaryl, or heterocylic, forming a 1,4- or 1,5-disubstitution; $R_3$=H or O; A, B, C, D, and E are each independently selected from C and N; Y=NH, O, or $CH_2$; and n=0, 1, 2, 3, 4, or 5.

Following the compounds discussed above, Scheme 4 (below) illustrates a broad presentation of a mechanism of synthesizing various compounds of the disclosure.

Scheme 4. Synthesis of various triazoles

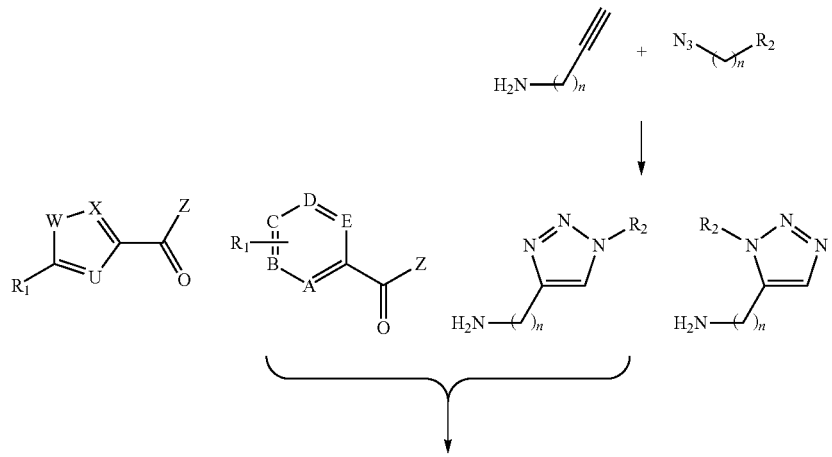

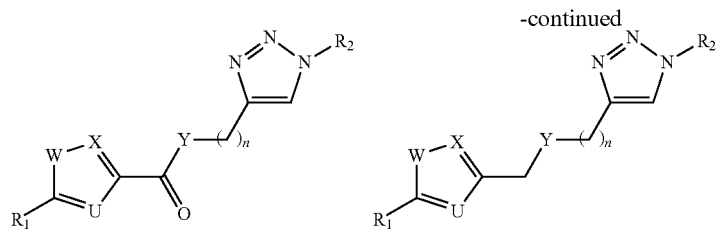
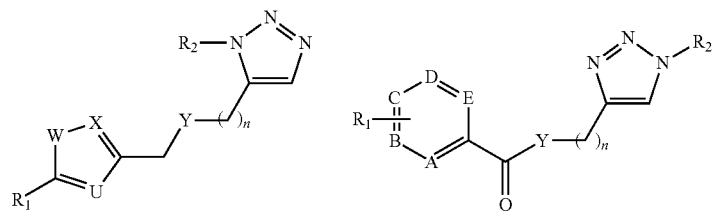
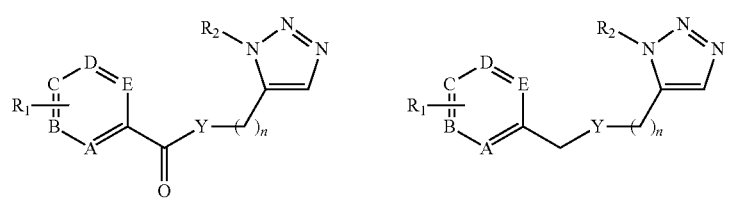

Z = H, Cl, OH, NCH₃OCH₃

Efficacy in inhibiting cancer cell growth was demonstrated, in some embodiments, using the National Cancer Institute Anti-cancer Drug Screen Assay. For additional details pertaining to the assay, see, for example, Shoemaker, R. H., The NCI60 Human Tumour Cell line Anticancer Drug Screen, Nature Reviews, 6: 813-823, 2006, the disclosure of which is hereby incorporated by reference in its entirety.

Briefly, the cell lines comprising the National Cancer Institute Anti-cancer Drug Screen panel were obtained and processed as described previously. After an initial acquisition, in vitro expansion was followed by cryopreservation of a large number of master stock samples, for serial rethawing at 20-passage intervals. The parental cells included the small cell lung carcinoma cell line UMCC-1, the human leukemia cell line HL-60, estrogen receptor-positive MCF7 and ZR-75B human breast carcinoma cells, and estrogen receptor-negative MDA-MB231 human breast carcinoma cells. The parental cells were grown in monolayers or in suspension in Eagle's minimum essential medium containing 10% fetal bovine serum, 2 mM L-glutamine, 100 units/ml penicillin, and 100 µg/ml streptomycin in 5% $CO_2$ at 37° C.

The current version of COMPARE is configured to calculate pairwise correlations with the $log_{10}$ of one of the specific National Cancer Institute cell line activity parameters $GI_{50}$, TGI, or $LC_{50}$. The $GI_{50}$ is the National Cancer Institute designation for a time zero-corrected $IC_{50}$ value and is defined as the concentration of an agent that causes a 50% growth inhibition. Thus, $log_{10}$ ($GI_{50}$ values) for a seed or probe compound is correlated with the corresponding data from each compound in a database. Table 1 shows the in vitro anticancer activity of two of the triazole compounds as compared to known chemotherapeutic agents.

TABLE 1

In vitro anti-cancer activity of triazoles 9c and 9f, vincristine, colchicine, and 2-methoxyestradiol against human breast cancer cell line MCF-7, human leukemia cell line HL-60, and a vincristine-resistant leukemia cell line, HL-60 VCR, that overexpresses p-glycoprotein.

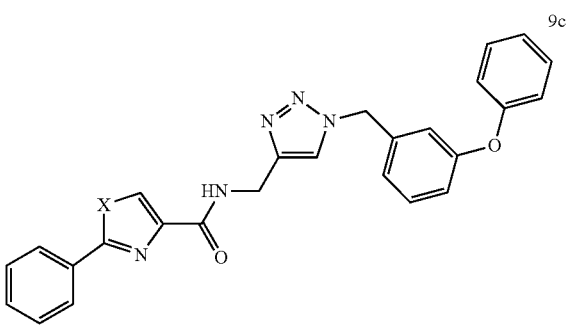

9c

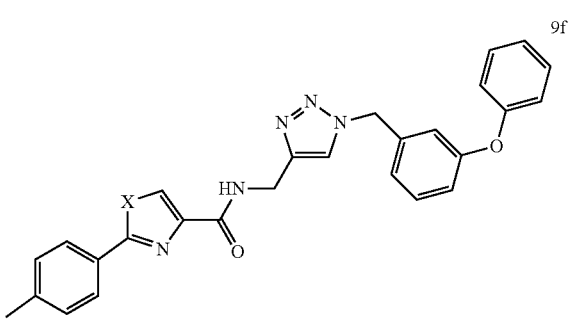

9f

| Compound | $IC_{50}$ (µM) | | |
|---|---|---|---|
| | MCF-7 | HL-60 | HL-60 VCR |
| 9c | 0.5 | 7.9 | 12.2 |
| 9f | 0.3 | 4.75 | >100 |
| vincristine[b] | 0.2 | 0.57 | >100 |

TABLE 1-continued

| | | | |
|---|---|---|---|
| colchicine[b] | 0.004 | 0.12 | >100 |
| 2-methoxyestradiol[c] | 1.3 | 9.15 | 48 |

[a]IC$_{50}$ values indicate in vitro anti-cancer activity.
[b]Vincristine and colchicine are known substrates for p-glycoprotein.
[c]2-methoxyestradiol is not a substrate for p-glycoprotein.

As shown in Table 1, the addition of the triazole moiety unexpectedly created potent anti-cancer activity in these compounds. This activity was more potent than that of known antimitotic agents vincristine, colchicine, and 2-methoxyestradiol. FIG. 1 shows the results of biological testing of compound 9c (ND-6732) when the NCI Assay results were analyzed for trends in cancer cell type selectivity. A mean graph of activity compares the relative activity of compound 9c (ND-6732) against all 60 cell lines in the NCI assay. Although all three compounds showed anti-cancer activity, compound 9c (ND-6732) was the most potent inhibitor of MCF7 cell growth.

Figure 2:
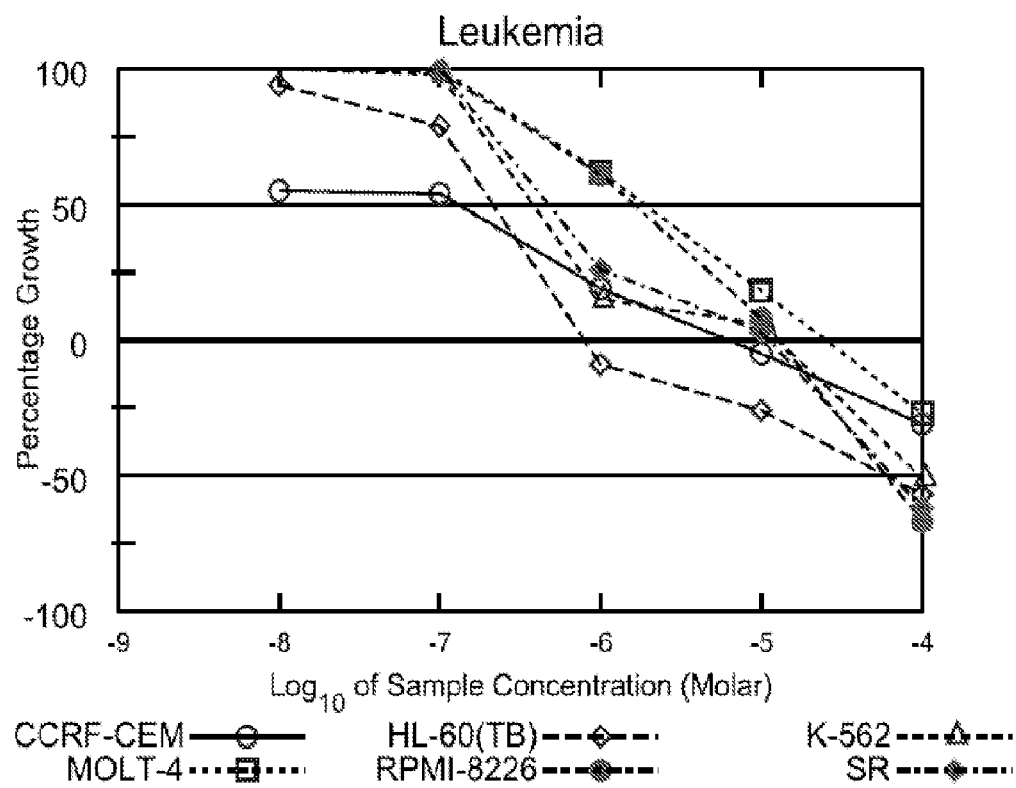
FIG. 2 illustrates the potent anti-cancer activity of various compounds disclosed herein in the NCI assay using multiple leukemia cell lines, in accordance with various embodiments.
Figure 3:
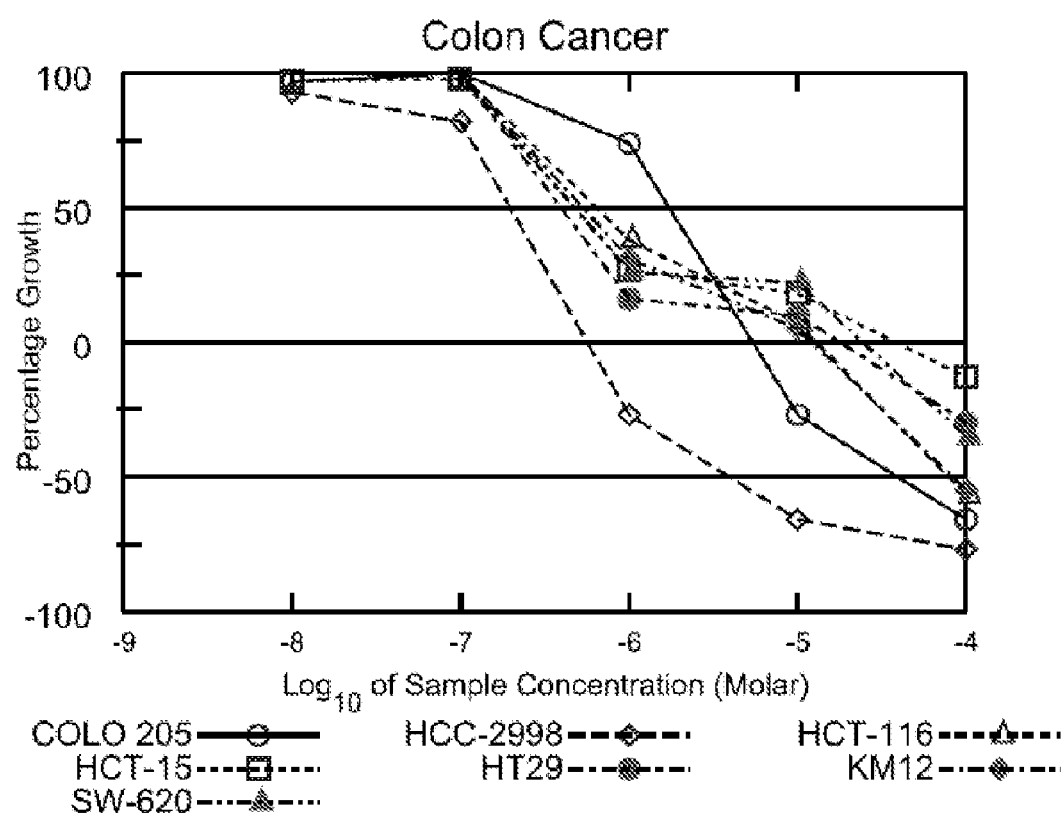
FIG. 3 illustrates the potent anti-cancer activity of various compounds disclosed herein in the NCI assay using multiple colon cancer cell lines, in accordance with various embodiments.

FIGS. 2 and 3 show that compound 9c (ND-6732) produced at least a 50% growth inhibition of multiple cell lines of leukemia (FIG. 2) and colon cancer (FIG. 3) when applied to the cells at nanomolar concentrations.

Table 2 shows the effect of truncation of the aryl ethyl moiety on the IC50 value of various compounds when applied to MCF7 cells using the NCI Anti-cancer Drug Screen Assay.

TABLE 2

SAR: Truncation of aryl ether moiety.

| | Compound | MCF7 IC$_{50}$ (µM) |
|---|---|---|
| 9c | [structure] | 0.50 |
| 9a | [structure] | 4.0 |
| 8a | [structure] | >20 |

Table 3 shows the effect of truncation of the aryl carboxamide moiety on the IC50 value of various 1,2,3-triazole compounds when applied to MCF7 cells using the NCI Drug Screen Assay.

TABLE 3

SAR: Truncation of aryl carboxamide moiety.

| | Compound | MCF7 IC$_{50}$ (µM) |
|---|---|---|
| 9c | [structure] | 0.50 |

TABLE 3-continued

SAR: Truncation of aryl carboxamide moiety.

| Compound | | MCF7 IC$_{50}$ (μM) |
|---|---|---|
| 15 | (oxazole-CONH-CH$_2$-triazole-CH$_2$-C$_6$H$_4$-O-C$_6$H$_5$) | 1.0 |
| 14 | (pyridine-2-CONH-CH$_2$-triazole-CH$_2$-C$_6$H$_4$-O-C$_6$H$_5$) | 0.07 |
| 16 | (phenyl-CONH-CH$_2$-triazole-CH$_2$-C$_6$H$_4$-O-C$_6$H$_5$) | 0.20 |
| 17 | (CH$_3$-CONH-CH$_2$-triazole-CH$_2$-C$_6$H$_4$-O-C$_6$H$_5$) | 6.0 |

Shown below in Table 4 are the results of the COMPARE analysis of compound 9c (ND-6732) as compared to several known anti-cancer agents.

TABLE 4

Standard COMPARE.

| Standard Agents GI$_{50}$ | | Standard Agents TGI | | Standard Agents LC$_{50}$ | |
|---|---|---|---|---|---|
| Correlation | Compound | Correlation | Compound | Correlation | Compound |
| 0.505 | Maytansine | 0.617 | Paclitaxel | 0.732 | Rhizoxin |
| 0.461 | Vincristine Sulfate | 0.615 | Vinblastine Sulfate | 0.652 | Maytansine |
| 0.452 | Paclitaxel | 0.611 | Maytansine | 0.639 | Rhizoxin (2) |

Various analogs of the oxazole triazole scaffold were prepared and tested for their anti-cancer activity in various cellular assays (testing was done as described previously). The result of this SAR (structure-activity-relationship) study is shown in Table 5 and the compound structures are displayed in Table 6.

TABLE 5

Anti-cancer data of various heterocyclic analogs.

| Name | ND ID # | IC50 (μM) MCF-7 (Breast) | PC-3 (Prostate) | RXF 393 (Renal) | CAKI-1 (Renal) | SR (Leukemia) |
|---|---|---|---|---|---|---|
| JAS-I-146B | ND-008174 | 3 | 10 | | | |
| JAS-I-150B | ND-008169 | 3 | 10 | | | |
| JAS-I-156A | ND-008171 | 15 | >100 | | | |
| JAS-I-166 | ND-008186 | 4 | 2.4 | | | |
| JAS-I-168 | ND-008183 | 13 | >50 | | | |
| RJP-1-20 | ND-006728 | 3.12 | 0.221 | 0.187 | 4.61 | >100 |
| RJP-1-21 | ND-006729 | 4.08 | 0.216 | 0.357 | 0.102 | 1.33 |
| RJP-1-22 | ND-006730 | 3.83 | >100 | 0.282 | 8.01 | 2.05 |
| RJP-1-23-2 | ND-006731 | 4.16 | 92.7 | 27 | 9.1 | 2.65 |
| RJP-1-25-2 | ND-006732 | 0.302 | 0.504 | 0.299 | 0.392 | 0.484 |
| RJP-1-34-3 | ND-006735 | 8.93 | 25.2 | 14.2 | 21 | 0.073 |
| CCO1-20-1 | ND-007883 | 7 | 20 | | | |
| CCO1-29-1 | ND-007885 | 8 | 12 | | | |
| CCO1-32-1 | ND-007887 | 0.937 | 1.25 | | | |
| JAS-I-171 | ND-008467 | 0.3 | 1 | | | |
| JAS-I-170 | ND-008465 | 8 | 20 | | | |
| JAS-I-173 | ND-008468 | 15 | 20 | | | |
| JAS-I-174 | ND-008469 | 20 | >20 | | | |
| JAS-I-175 | ND-008470 | >20 | >20 | | | |
| JAS-I-176 | ND-008471 | >20 | >20 | | | |
| JAS-I-181 | ND-008492 | 6 | 17 | | | |
| JAS-I-179 | ND-008493 | >20 | >20 | | | |
| JAS-I-189 | ND-008504 | 0.15 | 0.3 | | | |
| JAS-I-190 | ND-008505 | 1 | 1 | | | |
| JAS-I-188 | ND-008506 | 0.2 | 0.5 | | | |

TABLE 6

Compound Structures of Table 5.

| Compound ID | Name | Structure | Mol Wt | Formula |
|---|---|---|---|---|
| ND-006728 | RJP-1-20 | 2-phenyl-oxazole-4-carboxamide linked to 1-(2-methoxybenzyl)-1H-1,2,3-triazol-4-yl | 389.41 | C21H19N5O3 |
| ND-006729 | RJP-1-21 | 2-phenyl-oxazole-4-carboxamide linked to 1-(4-trifluoromethoxybenzyl)-1H-1,2,3-triazol-4-yl | 443.38 | C21H16F3N5O3 |
| ND-006730 | RJP-1-22 | 2-phenyl-oxazole-4-carboxamide linked to 1-(4-trifluoromethylbenzyl)-1H-1,2,3-triazol-4-yl | 427.38 | C21H16F3N5O2 |
| ND-006731 | RJP-1-23-2 | 2-phenyl-oxazole-4-carboxamide linked to 1-(3-methoxybenzyl)-1H-1,2,3-triazol-4-yl | 389.41 | C21H19N5O3 |

TABLE 6-continued

Compound Structures of Table 5.

| Compound ID | Name | Structure | Mol Wt | Formula |
|---|---|---|---|---|
| ND-006732 | RJP-1-25-2 | 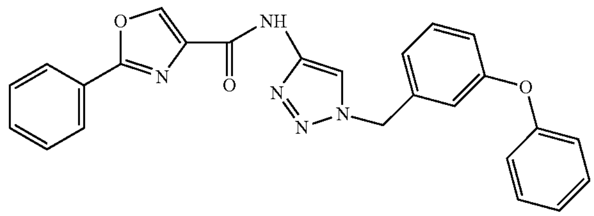 | 451.48 | C26H21N5O3 |
| ND-006735 | RJP-1-34-3 | 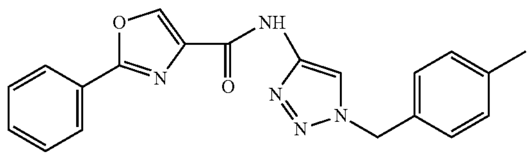 | 373.41 | C21H19N5O2 |
| ND-007883 | CCO1-20-1 | 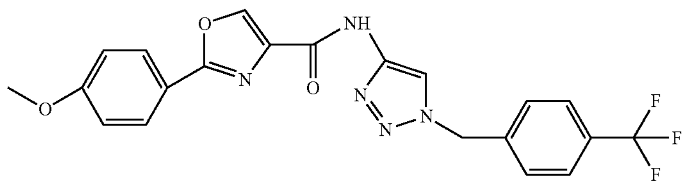 | 457.41 | C22H18F3N5O3 |
| ND-007885 | CCO1-29-1 | 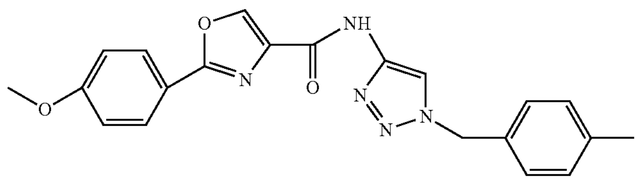 | 403.43 | C22H21N5O3 |
| ND-007887 | CCO1-32-1 | 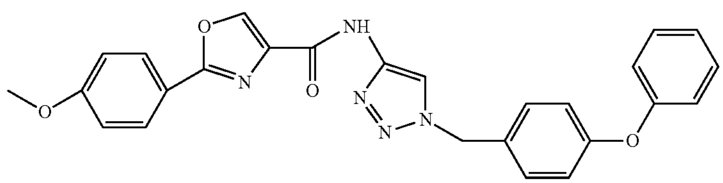 | 481.5 | C7H23N5O4 |
| ND-008169 | JAS-I-150B | 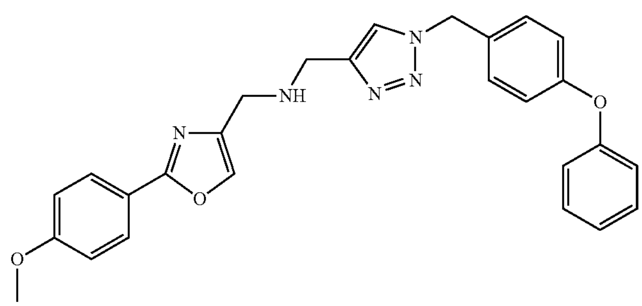 | 467.52 | C27H25N5O3 |
| ND-008171 | JAS-I-156A | 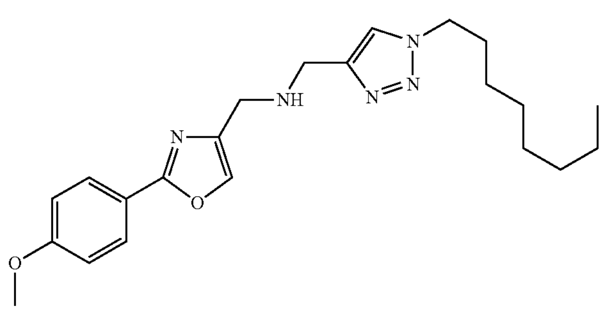 | 397.51 | C22H31N5O2 |

TABLE 6-continued

Compound Structures of Table 5.

| Compound ID | Name | Structure | Mol Wt | Formula |
|---|---|---|---|---|
| ND-008174 | JAS-I-146B | 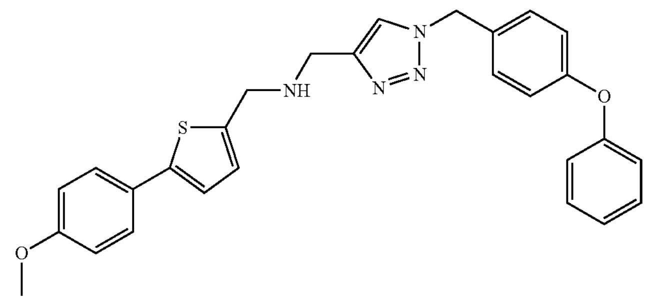 | 482.6 | C28H26N4O2S |
| ND-008183 | JAS-I-168 | 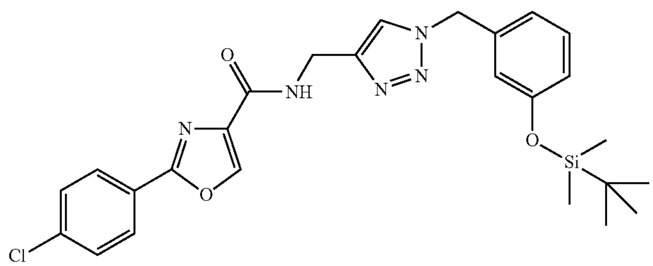 | 524.09 | C26H30ClN5O3Si |
| ND-008186 | JAS-I-166 | 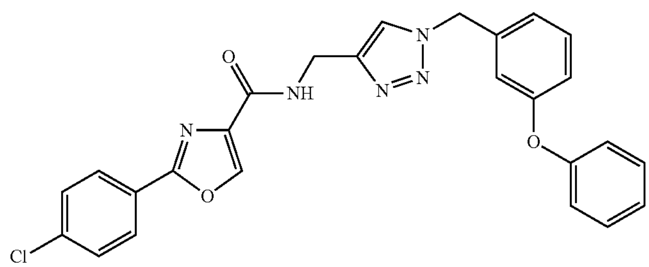 | 485.92 | C26H20ClN5O3 |
| ND-008485 | JAS-I-170 | 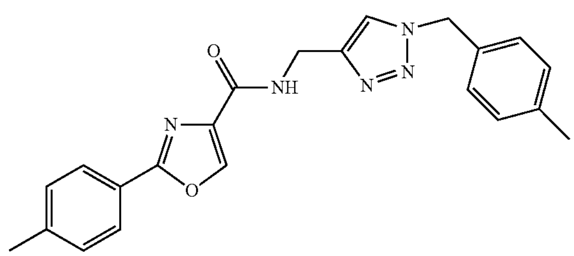 | 387.43 | C22H21N5O2 |
| ND-008467 | JAS-I-171 | 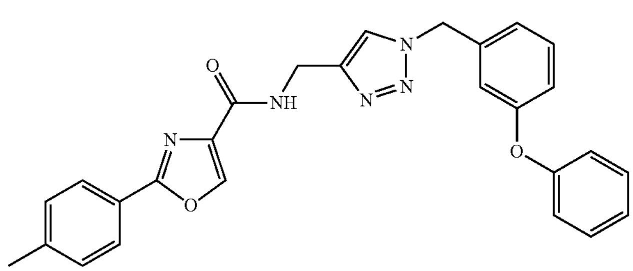 | 465.5 | C27H23N5O3 |

TABLE 6-continued

Compound Structures of Table 5.

| Compound ID | Name | Structure | Mol Wt | Formula |
|---|---|---|---|---|
| ND-008468 | JAS-I-173 | 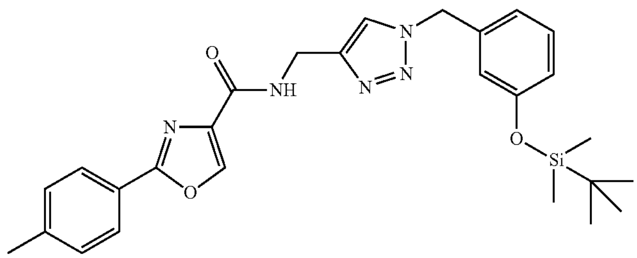 | 503.67 | C27H33N5O3Si |
| ND-008469 | JAS-I-174 | 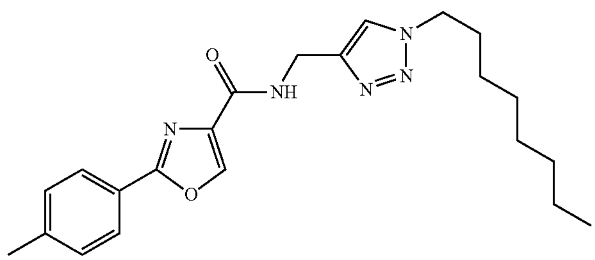 | 395.5 | C22H29N5O2 |
| ND-008470 | JAS-I-175 | 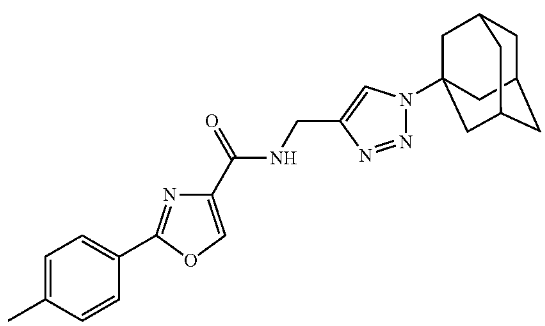 | 417.5 | C24H27N5O2 |
| ND-008471 | JAS-I-176 | 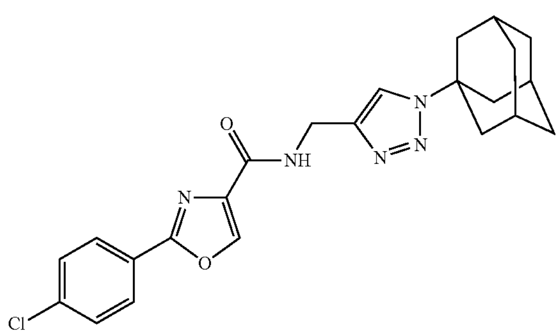 | 437.92 | C23H24ClN5O2 |
| ND-008492 | JAS-I-181 | 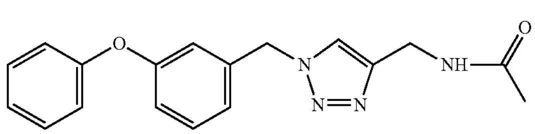 | 322.36 | C18H18N4O2 |
| ND-008493 | JAS-I-179 | 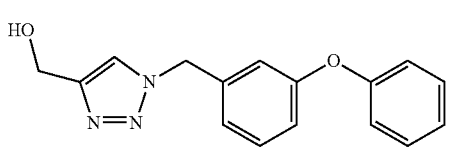 | 281.31 | C16H15N3O2 |

TABLE 6-continued

Compound Structures of Table 5.

| Compound ID | Name | Structure | Mol Wt | Formula |
|---|---|---|---|---|
| ND-008504 | JAS-I-189 | 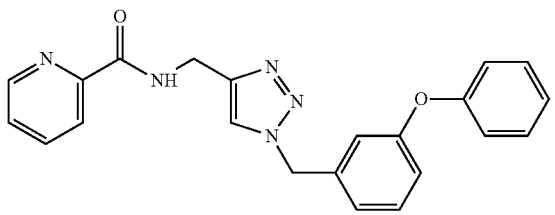 | 385.42 | C22H19N5O2 |
| ND-008505 | JAS-I-190 | 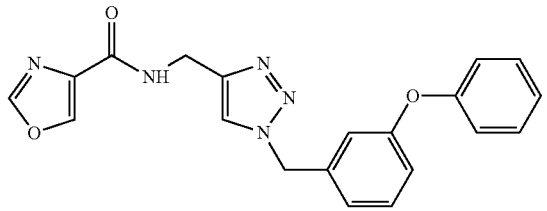 | 375.38 | C20H17N5O3 |
| ND-008506 | JAS-I-188 | 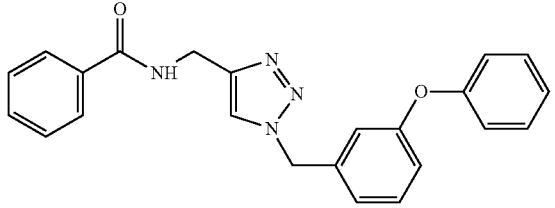 | 384.43 | C23H20N4O2 |

Figure 4:
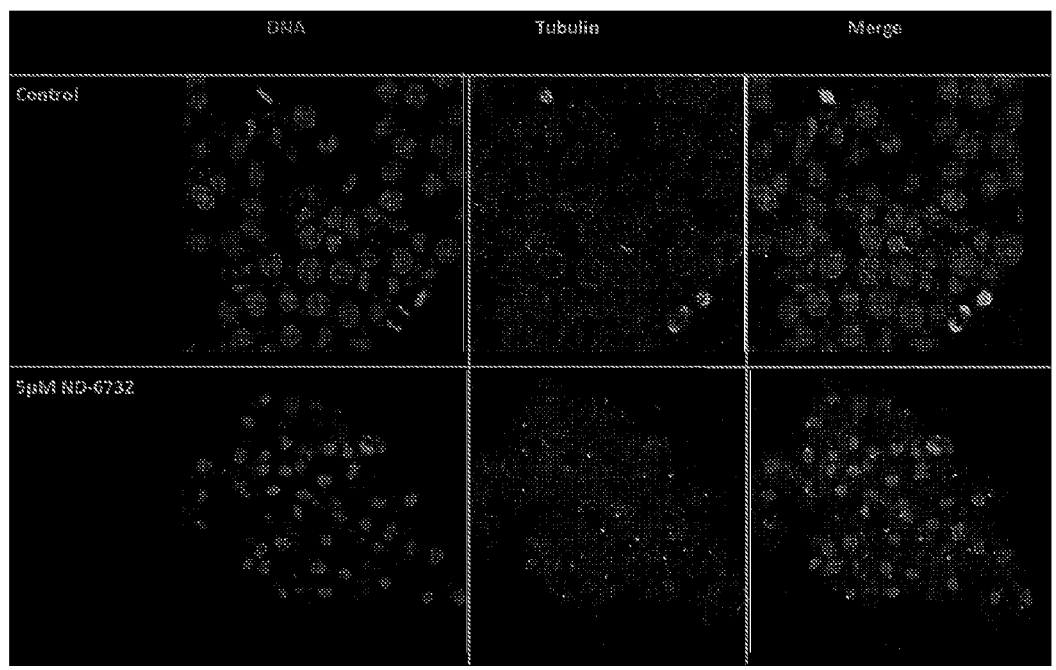
FIG. 4 is a digital confocal microscopy image of HeLa cells treated with 1,2,3-triazole 9c (ND-6732), in accordance with various embodiments.
Figure 5:
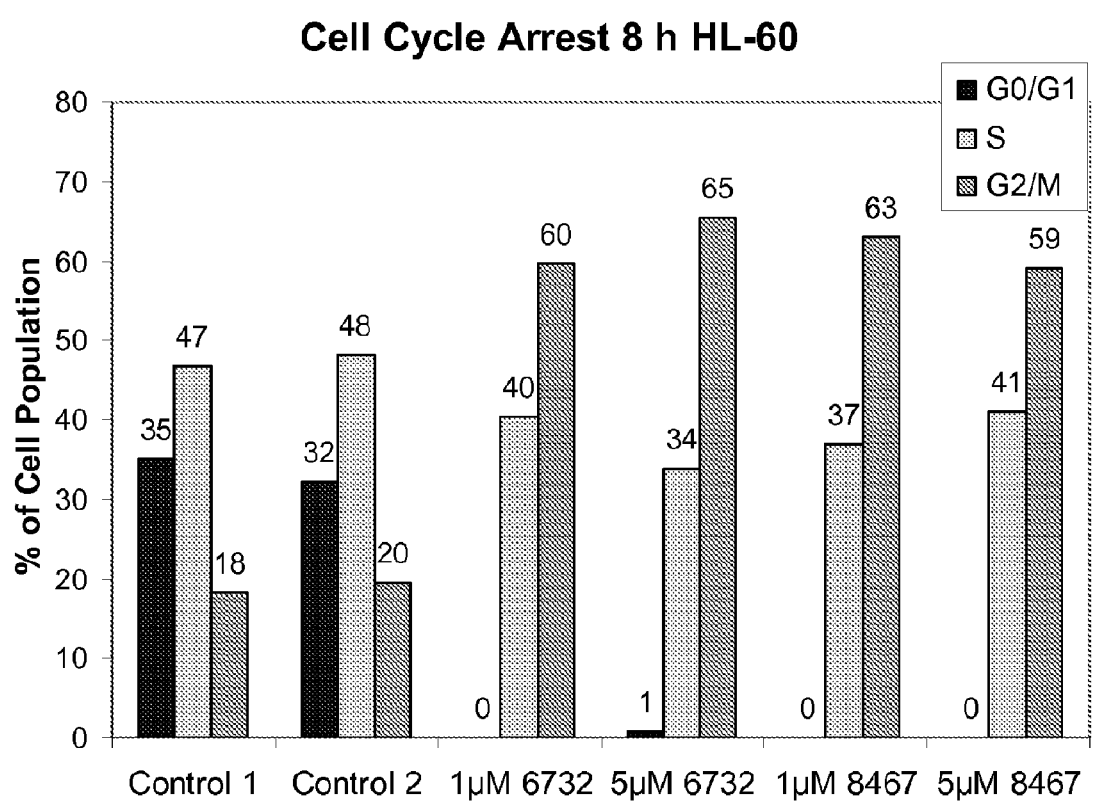
FIG. 5 illustrates cell cycle arrest showing $G_2$/M-phase arrest in cells treated with 1,2,3-triazole 9c (ND-6732), in accordance with various embodiments.
Figure 6:
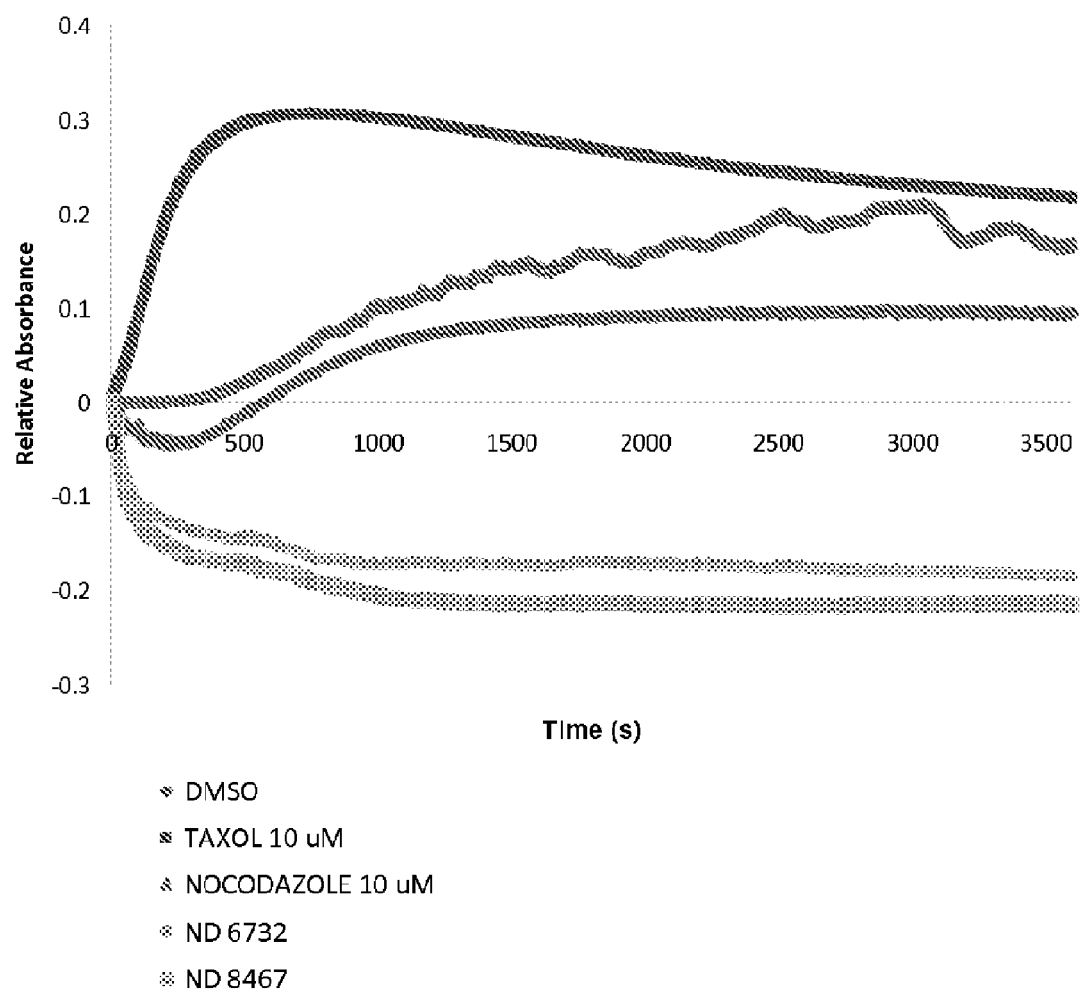
FIG. 6 illustrates a tubulin polymerization assay, which showed potent inhibition of tubulin polymerization by the 1,2,3-triazoles, according to various embodiments.

Without being bound by theory, it is believed that the anti-cancer activity of various disclosed compounds disclosed herein is due to antimitotic activity. As shown in FIG. 4, confocal microscopy of cells treated with the 1,2,3-triazoles showed fragmented mitotic spindles, which is characteristic of antimicrotubule compounds. In agreement with these results, FIG. 5 shows that compound 9c (ND-6732) results in cell cycle arrest at the G2M phase of mitosis. FIG. 6 shows the results of a tubulin polymerization assay, which demonstrates potent inhibition of tubulin polymerization by the 1,2,3-triazoles (FIG. 4).

In another embodiment, a method for treating cancer in a subject is provided. The method includes selecting a subject having or at risk for developing a cancer that responds to antimitotic therapy, and administering to the subject a therapeutically effective dose of at least one compound disclosed herein.

Although the anti-cancer compounds disclosed herein can be used to treat a wide variety of cancers in animal and human subjects, the compounds are particularly effective at treating CNS cancers such as neuroblastomas, renal cell cancers, melanomas, leukemias, colon cancers, breast cancers, ovarian cancers, prostate cancers, and non-small cell lung cancers.

As used herein, the term "therapeutically effective amount" includes a quantity of a specified compound (such as one of the oxazole- or triazole-containing anti-cancer agents disclosed herein, for instance compound 9c (ND-6732)) required to achieve a desired effect in a subject being treated. For instance, this may be the amount necessary to treat a cancer, such as a CNS cancer, melanoma, renal cell cancer, leukemia, colon cancer, breast cancer, ovarian cancer, prostate cancer, or non-small cell lung cancer in a subject, or a dose sufficient to prevent advancement, or to cause regression of a disease (such as the tumor), or which is capable of relieving symptoms caused by a disease, such as pain, inflammation, neurological symptoms, or fatigue.

Various dosage ranges and administration schedules may be adopted for therapeutic treatment of cancers in animal and human subjects with the anti-cancer agents disclosed herein. In an embodiment, such a therapeutically effective amount of active component may be in the range of about 0.1 to about 100 mg/kg, or more preferably about 3.0 to about 50 mg/kg, of body weight/day. Such dosages may vary depending upon the requirements of the patient, the severity, type, stage, grade, or location of the cancer being treated, and the particular compound being used.

In some embodiments, the anti-cancer agent may be administered in conjunction with one or more other anti-cancer agents, such as alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and bbr3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin;

topoisomerase inhibitors, such as topotecan and irinotecan; monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; cytokines, such as IL-2 and IL-27; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In some embodiments, the anti-cancer agent (for instance, compound 9c (ND-6732)) may be administered systemically, whereas in other embodiments the anti-cancer agent may be administered locally. An effective dose of a disclosed anti-cancer agent may be administered systemically in a variety of ways. For instance, systemic administration may be by injection, for instance intravenous, intra-arterial, subcutaneous, intramuscular, or intra-peritoneal injection. Systemic administration also may include transdermal or inhalational administration. By way of example, one method of administration to the lungs of an individual may be by inhalation through the use of a nebulizer or inhaler. For example, the anti-cancer agent may be formulated in an aerosol or particulate and drawn into the lungs using a standard nebulizer well known to those skilled in the art. Transdermal administration may be accomplished, for example, by application of a topical cream or ointment or by using a transdermal patch.

An effective amount of an anti-cancer agent may be administered in a single dose, or in multiple doses, for example daily, or every four, eight, or twelve hours, during a course of treatment. In one embodiment, a therapeutically effective amount of an anti-cancer agent may be administered as a single pulse dose, as a bolus dose, or as pulse doses administered over time. In specific, non-limiting examples, pulse doses of an anti-cancer agent may be administered during the course of a day, during the course of a week, or during the course of a month. In some embodiments, the anti-cancer agent may be administered to the subject on a schedule that includes several daily doses of the anti-cancer agent, followed by a withdrawal period, for example to reduce toxicity. For instance, in certain embodiments, the anti-cancer agent may be administered daily for two, three, four, five, six, seven, or more days in a row, followed by a period in which the drug may not be administered for one, two, three, four, five, six, seven, or more days. This cycle may be repeated until the desired therapeutic effect is achieved, for example tumor regression or remission. In certain examples, the cycle may be repeated from about two to about ten times, or even more.

In some embodiments, the anti-cancer agent may be administered locally. In certain embodiments, this may be accomplished by local injection into the body part that is affected by the cancer, for example by injecting or infusing the anti-cancer agent directly into the tumor. In other embodiments, local administration may be accomplished by implanting a sustained-release device such as a pump or a micropump, or sustained-release implant, such as a bead or gel that contains the anti-cancer agent and slowly releases the drug into the desired area over time.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A compound having the formula

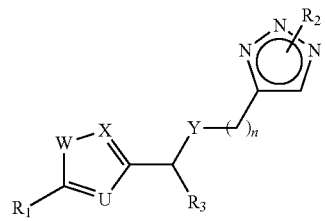

or a pharmaceutically acceptable salt thereof, wherein $R_1$=H, halogen, alkyl, substituted alkyl, cycloalkyl, cycloheteroalkyl, acyl, halogenated acyl, substituted acyl, aryl, substituted aryl, heteroaryl, substituted heteroaryl, or heterocylic, wherein $R_1$ is mono or polysubstituted;

$R_2$=H, alkyl, substituted alkyl, cycloalkyl, aryl, heteroaryl, substituted heteroaryl, or heterocylic, forming a 1,4- or 1,5-disubstitution;

$R_3$=H or O;

Y=NH, O, or $CH_2$;

U, W, and X are each independently selected from C, O, S, NH, or $NR_1$; and n=0, 1, 2, 3, 4, or 5.

2. The compound of claim 1, wherein $R_1$ is a substituted alkyl, and wherein the substituted alkyl comprises an alkene, an alkyne, an alcohol, an epoxide, a ketone, an ester, an ether, an aldehyde, a nitrile, a nitro, a thiol, a thioester, a sulfide, a disulfide, a sulfone, a sulfoxide, an amine, an amide, a urea, or a carbamate.

3. The compound of claim 1, wherein $R_1$ is a cycloheteroalkyl, and wherein the cycloheteroalkyl comprises a morpholine, a thiomorpholine, a piperazine, or a piperidine.

4. The compound of claim 1, wherein $R_1$ is a heterocyclic, and wherein the heterocyclic comprises a furan, a nitrofuran, a thiophene, a nitrothiophene, an imidazole, an oxazole, an oxazoline, a thiazole, a thiazoline, a triazole, a pyridine, a pyrazine, a naphthalene, a diketopiperazine, a quinoline, an isoquinoline, an imidazopyridine, an oxazolindinone or a substituted furan, nitrofuran, thiophene, nitrothiophene, imidazole, oxazole, oxazoline, thiazole, thiazoline, triazole, pyridine, pyrazine, naphthalene, diketopiperazine, quinoline, isoquinoline, imidazopyridines, or oxazolindinone.

5. The compound of claim 1, wherein $R_2$ is a substituted alkyl, and wherein the substituted alkyl comprises an alkene, an alkyne, an alcohol, an epoxide, a ketone, an ester, an ether, an aldehyde, a thiol, a sulfide, a disulfide, a sulfone, a sulfoxide, an amine, an amide, a urea, or a carbamate.

6. The compound of claim 1, wherein $R_2$ is O, W is O, and U is N.

7. The compound of claim 1, wherein the compound has formula:
A.
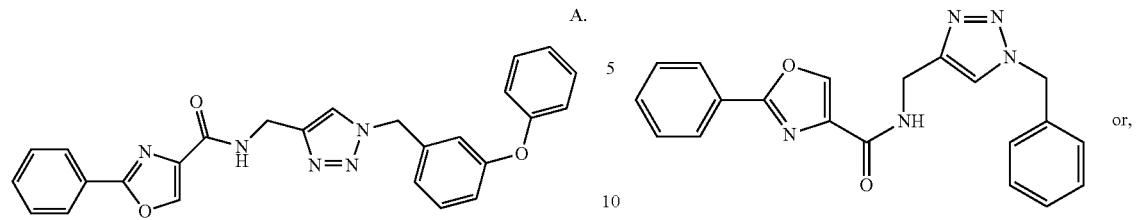
B.
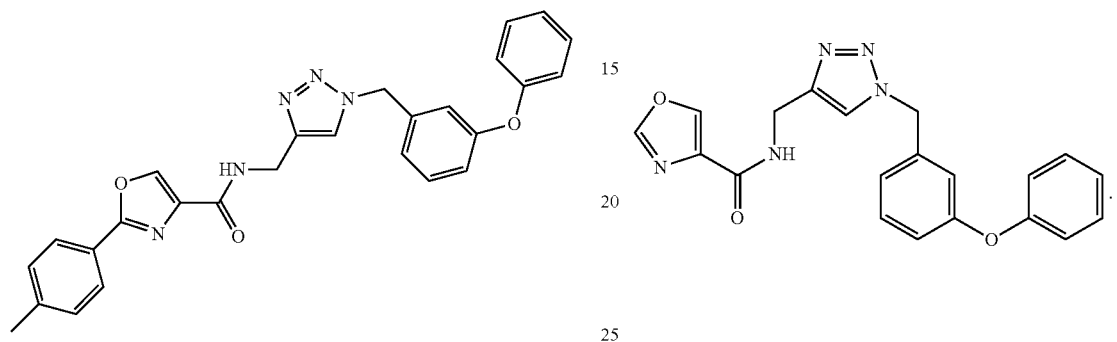
C.
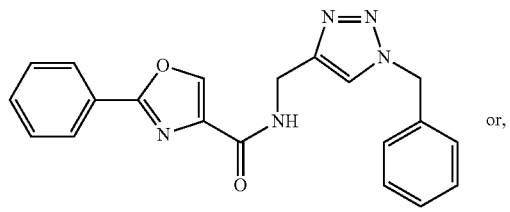
or,
D.
* * * * *